United States Patent

Taketomi et al.

Patent Number: 4,906,773
Date of Patent: Mar. 6, 1990

[54] PROCESS FOR PREPARING OPTICALLY ACTIVE THREONINE

[75] Inventors: Takanao Taketomi, Chiba; Hidenori Kumobayashi, Kanagawa, both of Japan

[73] Assignee: Takasago International Corporation, Tokyo, Japan

[21] Appl. No.: 287,434

[22] Filed: Dec. 21, 1988

[30] Foreign Application Priority Data

Dec. 22, 1987 [JP] Japan .................................. 62-324399

[51] Int. Cl.[4] ............................................. C07C 99/00
[52] U.S. Cl. ..................................................... 562/570
[58] Field of Search .......................... 562/570; 560/170

[56] References Cited

FOREIGN PATENT DOCUMENTS 2804892  8/1978  Fed. Rep. of Germany .

*Primary Examiner*—Michael L. Shippen
*Attorney, Agent, or Firm*—Sughrue, Mion, Zinn, Macpeak & Seas

[57] ABSTRACT

A process for preparing optically active threonine is disclosed, which comprises asymmetrically hydrogenating a 2-N-acylaminoacetoacetic ester represented by formula (I):

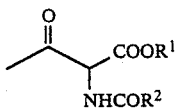

(I)

wherein $R^1$ represents a lower alkyl group, a phenyl group, a phenyl group substituted with a lower alkyl group or a lower alkoxy group, a benzyl group, or a benzyl group substituted with a lower alkyl group or a lower alkoxy group; $R^2$ represents a hydrogen atom, a lower alkyl group, a lower alkoxy group, a phenyl group, a phenyl group substituted with a lower alkyl group or a lower alkoxy group, a benzyloxy group, or a benzyloxy group substituted with a lower alkyl group or a lower alkoxy group, in the presence of a ruthenium-optically active phosphine complex as a catalyst to obtain an optically active threonine derivative represented by formula (II):

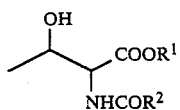

(II)

wherein $R^1$ and $R^2$ are as defined above, and then hydrolyzing the compound of formula (II). The 2-N-acylaminoacetoacetic ester intermediate can be selectively prepared in a high yield. Either natural type threonine or non-natural type threonine can be prepared selectively by selecting the absolute configuration of the ligand of the ruthenium-optically active phosphine complex.

2 Claims, No Drawings

PROCESS FOR PREPARING OPTICALLY ACTIVE THREONINE

FIELD OF THE INVENTION

This invention relates to a process for preparing optically active threonine which is important as an essential amino acid and also useful as an intermediate for synthesizing pharmaceuticals, by asymmetric hydrogenation of a 2-N-acylaminoacetoacetic ester in the presence of a ruthenium-optically active phosphine complex as a catalyst, followed by hydrolysis. The process of this invention can make a distinction of the product between natural type threonine and non-natural type threonine by properly selecting the absolute configuration of the ligand of the ruthenium-optically active phosphine complex used.

BACKGROUND OF THE INVENTION

There have been proposed many processes for preparing optically active threonine. The typical one comprises synthesizing DL-threonine and then optically resolving the racemate with an enzyme to obtain the desired isomer, the undesired isomer being reused through racemization, as described in Fodor, et al., *J. Biol. Chem.*, Vol. 178, 503 (1949).

A problem in the conventional synthesis of threonine lies in the difficulty of selectively synthesizing a threo form. That is, the product obtained generally comprises a mixture of a threo form and an erythro form at a ratio of 8 to 2. Another problem is that since each of the threo form and the erythro form comprises optical isomers (antipodes), isolation of the respective desired isomers cannot be achieved without racemic resolution. This means that the whole process involves a step for separating and purifying the isomer and a step for racemizing the undesired isomer, thus leading to an increase of production cost.

SUMMARY OF THE INVENTION

As a result of extensive investigations with the purpose of settling the above-described problems and meeting demands in the art, the inventors have found that an optically active N-acylthreonine can be synthesized selectively in high yield by hydrogenation of a 2-N-acylaminoacetoacetic ester in the presence of a ruthenium-optically active phosphine complex as a catalyst. This process has been confirmed capable of synthesizing either natural type threonine or non-natural type threonine arbitrarily by selecting the absolute configuration of the ligand of the ruthenium-optically active phosphine complex. The present invention has been completed based on these findings.

The present invention relates to a process for preparing optically active threonine which comprises asymmetrically hydrogenating a 2-N-acylaminoacetoacetic ester represented by formula (I):

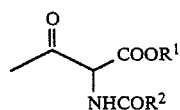

wherein $R^1$ represents a lower alkyl group, a phenyl group, a phenyl group substituted with a lower alkyl group or a lower alkoxy group, a benzyl group, or a benzyl group substituted with a lower alkyl group or a lower alkoxy group; $R^2$ represents a hydrogen atom, a lower alkyl group, a lower alkoxy group, a phenyl group, a phenyl group substituted with a lower alkyl group or a lower alkoxy group, a benzyloxy group, or a benzyloxy group substituted with a lower alkyl group or a lower alkoxy group, in the presence of a ruthenium-optically active phosphine complex as a catalyst to obtain an optically active threonine derivative represented by formula (II):

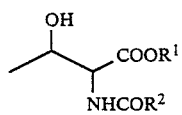

wherein $R^1$ and $R^2$ are as defined above, and then hydrolyzing the compound of formula (II).

DETAILED DESCRIPTION OF THE INVENTION

The 2-N-acylaminoacetoacetic ester represented by formula (I) which can be used in the present invention as a starting compound can be obtained by known processes, for example, the process described in Shulgin, et al., *J. Am. Chem. Soc.*, Vol. 74, 2427 (1952) and Attenburrow, et al., *J. Chem. Soc.*, 310 (1948). Specific but non-limiting examples of the compound of formula (I) includes methyl 2-N-accetamidoacetoacetate, ethyl 2-N-acetamidoacetoacetate, n-butyl 2-N-acetamidoacetoacetate, t-butyl 2-N-acetamidoacetoacetate, benzyl 2-N-acetamidoacetoacetate, p-methoxybenzyl 2-N-acetamidoacetoacetate, p-methylbenzyl 2-N-acetamidoacetoacetate, methyl 2-N-benzamidoacetoacetate, ethyl 2-N-benzamidoacetoacetate, benzyl 2-N-benzamidoacetoacetate, ethyl 2-N-benzyloxycarbonylamidoacetoacetate, methyl 2-N-ethoxycarbonylamidoacetoacetate, ethyl 2-N-t-butoxycarbonylamidoacetoacetate, benzyl 2-N-benzyloxycarbonylamido acetoacetate, methyl 2-N-formamidoacetoacetate, benzyl 2-N-formamidoacetoacetate, and t-butyl 2-N-formamidoacetoacetate.

The ruthenium-optically active phosphine complex to be used as a catalyst includes those represented by the following formulae (III), (V), (VI), and (VII):

$$Ru_xH_yCl_z(R^3\text{-BINAP})_2(T)_p \qquad (III)$$

wherein $R^3$-BINAP represents a tertiary phosphine represented by formula (IV):

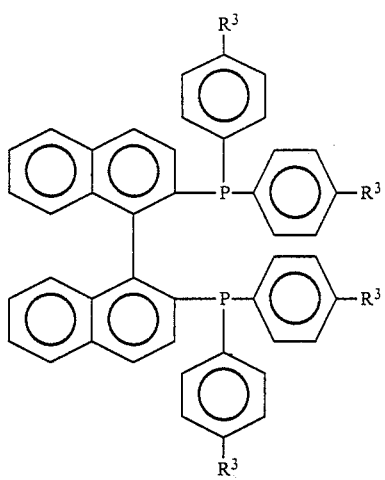 (IV)

wherein $R^3$ represents a hydrogen atom, a methyl group, or a t-butyl group; T represents a tertiary amine; when y represents 0, x represents 2, z represents 4, and p represents 1; and when y represents 1, x represents 1, z represents 1, and p represents 0.

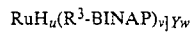

wherein $R^3$-BINAP is as defined above; Y represents $ClO_4$, $BF_4$ or $PF_6$; when u represents 0, v represents 1, and w represents 2; and when u represents 1, v represents 2, and w represents 1.

 (VI)

wherein $R^3$-BINAP is as defined above; and $R^4$ represents a lower alkyl group or a trifluoromethyl group.

 (VII)

wherein $R^3$-BINAP is as defined above; M represents Zn, Al, Ti, or Sn; X represents $N(C_2H_5)_3$ or $CH_3CO_2$; when X is $N(C_2H_5)_3$, l is 2, m is 1, and k is 4 when M is Zn, 5 when M is Al, or 6 when M is Ti or Sn; and when X is $CH_3CO_2$, l is 1, m is 2, and k is 2 when M is Zn, 3 when M is Al, or 4 when M is Ti or Sn.

The complex of formula (III) can be obtained by the process disclosed in T. Ikariya, et al., *J. Chem. Soc., Chem. Commun.*, 922–924 (1985) and JP-A-61-63690 (the term "JP-A" as used herein means an "unexamined published Japanese patent application"). More specifically, the complex of formula (III) wherein y is 0 can be prepared by reacting 1 mole of $[RuCl_2(COD)]_n$ (wherein COD represents cycloocta-1,5-diene, hereinafter the same), which is obtainable by reacting ruthenium chloride and COD in an ethanol solution, and 1.2 mols of a 2,2'-bis(di-p-$R^3$-phenylphosphino)-1,1'-binaphthyl ($R^3$-BINAP) by heating in a solvent (e.g., toluene, ethanol) in the presence of 4 moles of a tertiary amine (e.g., triethylamine). The complex of formula (III) wherein y is 1 can be prepared by reacting 1 mole of $[RuCl_2(COD)]_n$, 2.25 moles of $R^3$-BINAP, and 4.5 moles of a tertiary amine.

The complex of formula (V) wherein u is 0, v is 1, and w is 2 can be prepared by reacting $Ru_2Cl_4(R^3$-BINAP$)_2$(NEt$_3$) (wherein Et represents an ethyl group, hereinafter the same), which is obtained by the above-described process, with a salt represented by formula (VIII):

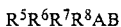 (VIII)

wherein M represents Na, K, Li, Mg, or Ag; and Y is as defined above, in a solvent system comprising water and methylene chloride in the presence of a quaternary ammonium salt or quaternary phosphonium salt represented by formula (IX):

$$R^5R^6R^7R^8AB \qquad (IX)$$

wherein $R^5$, $R^6$, $R^7$, and $R^8$ each represents an alkyl group having from 1 to 16 carbon atoms, a phenyl group, or a benzyl group; A represents a nitrogen atom or a phosphorus atom; and B represents a halogen atom, as a phase transfer catalyst. The reaction can be carried out by adding the reactants and the phase transfer catalyst of formula (IX) to a mixed solvent of water and methylene chloride and stirring the system. The amounts of the salt of formula (VIII) and the phase transfer catalyst of formula (IX) to be added range from 2 to 10 moles (preferably 5 moles) and from 1/100 to 1/10 mole, respectively, per mole of ruthenium. The reaction sufficiently proceeds by stirring at a temperature of from 5° to 30° C. for a period of from 6 to 18 hours, usually 12 hours. Examples of the phase transfer catalyst of formula (IX) are described in literature, e.g., W. P. Weber and G. W. Gokel, *Sokan Ido Shokubai (Japanese translation)*, 1st Ed., Kagaku Dojinsha (1978). After completion of the reaction, the reaction mixture is allowed to stand still, and the aqueous layer is removed by liquid-liquid separation. The methylene chloride solution thus separated is washed with water, and the methylene chloride is removed by distillation under reduced pressure to obtain the desired compound.

The complex of formula (V) where u is 1, v is 2, and w is 1 can be prepared by reacting $RuHCl(R^3$-BINAP$)_2$ with the salt of formula (VIII) in a mixed solvent of water and an organic solvent, e.g., methylene chloride, in the presence of the phase transfer catalyst of formula (IX). The amounts of the salt of formula (VIII) and the phase transfer catalyst of formula (IX) range from 2 to 10 moles (preferably 5 mole) and from 1/100 to 1/10 mole, respectively, per mole of ruthenium. This reaction sufficiently proceeds by stirring at a temperature of from 5° to 30° C. for a period of from 6 to 18 hours, usually 12 hours.

The complex of formula (VI) can be prepared by reacting $Ru_2Cl_4(R^3$-BINAP$)_2$(NEt$_3$) with a carboxylic acid salt in an alcohol solvent, e.g., methanol, ethanol, and t-butanol, at a temperature of from about 20° to 110° C. for 3 to 15 hours. After the reaction, the solvent is removed by distillation, and the residue is extracted with a solvent, e.g., diethyl ether, ethanol, etc., to obtain the desired complex, followed by concentration to dryness to obtain a crude complex. Recrystallization of the crude product from ethyl acetate, etc., gives a purified product. The acyloxy group ($R_4$=alkyl group) to be introduced can be determined by selecting the carboxylic acid to be used. For example, when sodium acetate is used as a carboxylic acid salt, $Ru(R^3$-BINAP)(OCOCH$_3$)$_2$ is yielded. The complex of formula (VI) having a trifluoroacetyl group ($R^4$=trifluoromethyl group) can be obtained by reacting the above-prepared diacetate complex with trifluoroacetic acid in methylene chloride at about 25° C. for about 12 hours.

The complex of formula (VII) can be prepared by starting with $Ru_2Cl_4(R^3\text{-BINAP})_2(NEt_3)$ or $Ru(R^3\text{-BINAP})\text{-}(OCOCH_3)_2$. That is, $Ru_2Cl_4(R^3\text{-BINAP})_2\text{-}(NEt_3)$ is reacted with a Lewis acid selected from zinc chloride, aluminum chloride, titanium tetrachloride, and tin tetrachloride in a solvent, e.g., methylene chloride, at 10° to 25° C. for 2 to 20 hours, and the solvent is removed by distillation, followed by drying to solidify to obtain the desired compound. $Ru(R^3\text{-BINAP})\text{-}(OCOCH_3)_2$ is reacted with the above-recited Lewis acid in a solvent, e.g., methylene chloride, at 10° to 25° C. for 2 to 20 hours, and the solvent is removed by distillation, followed by drying to solidify to obtain the desired compound.

In the processes stated above, an optically active ruthenium-phosphine complex can be obtained by using $R^3$-BINAP having the corresponding optical activity.

Specific examples of the ruthenium-optically active phosphine complex according to the present invention are shown below.

$Ru_2Cl_4(BINAP)_2(NEt_3)$
[BINAP represents 2,2'-bis(diphenylphosphino)1,1'-binaphthyl, hereinafter the same)
$Ru_2Cl_4(T\text{-BINAP})_2(NEt_3)$
[T-BINAP represents 2,2'-bis(di-p-tolylphosphino)-1,1'-binaphthyl]
$Ru_2Cl_4(t\text{-Bu-BINAP})_2(NEt_3)$
[t-Bu-BINAP represents 2,2'-bis(di-p-t-butyl-phenyl-phosphino)-1,1'- binaphthyl]
$RuHCl(BINAP)_2$
$RuHCl(T\text{-BINAP})_2$
$RuHCl(t\text{-Bu-BINAP})_2$
$[Ru(BINAP)](ClO_4)_2$
$[Ru(T\text{-BINAP})](ClO_4)_2$
$[Ru(t\text{-Bu-BINAP})](ClO4)_2$
$[Ru(BINAP)](BF_4)_2$
$[Ru(T\text{-BINAP})](BF_4)_2$
$[Ru(t\text{-Bu-BINAP})](BF_4)_2$
$[Ru(BINAP)](PF_6)_2$
$[Ru(T\text{-BINAP})](PF_6)_2$
$[RuH(BINAP)_2]ClO_4$
$[RuH(T\text{-BINAP})_2]ClO_4$
$[RuH(BINAP)_2]BF_4$
$[RuH(T\text{-BINAP})_2]BF_4$
$[RuH(BINAP)_2]PF_6$
$[RuH(T\text{-BINAP})_2]PF_6$
$Ru(BINAP)(OCOCH_3)_2$
$Ru(BINAP)(OCOCF_3)_2$
$Ru(T\text{-BINAP})(OCOCH_3)_2$
$Ru(BINAP)(OCO\text{-}t\text{-Bu})_2$
(t-Bu represents a t-butyl group)
$Ru(T\text{-BINAP})(OCOCF_3)_2$
$Ru(t\text{-Bu-BINAP})(OCOCH_3)_2$
$[Ru(BINAP)ZnCl_4]_2(NEt_3)$
$[Ru(BINAP)A;Cl_5]_2(NEt_3)$
$[Ru(BINAP)SnCl_6]_2(NEt_3)$
$[Ru(BINAP\ (NEt_3)$
$[Ru(T\text{-BINAP})ZnCl_4]_2(NEt_3)$
$[Ru(T\text{-BINAP})AlCl_5]_2(NEt_3)$
$[Ru(T\text{-BINAP})\ NEt_3)$
$[Ru(T\text{-BINAPTiCl}_6]_2NEt_3)$
$[Ru(BINAP)ZnCl_2](OCOCH_3)_2$
$[Ru(BINAP)AlCl_3](OCOCH_3)_2$
$[Ru(BINAP)SnCl_4](OCOCH_3)_2$
$[Ru(BINAP)TiCl_4](OCOCH_3)_2$
$[Ru(T\text{-BINAP})ZnCl_2](OCOCH_3)_2$
$[Ru(T\text{-BINAP})AlCl_3](OCOCH_3)_2$
$[Ru(T\text{-BINAP})SnCl_4](OCOCH_3)_2$
$[Ru(T\text{-BINAP})TiCl_4](OCOCH_3)_2$ In carrying out the present invention, a solution of a 2-N-acylaminoacetoacetic ester dissolved in an equivalent amount to ten times the volume of a solvent, e.g., methanol, ethanol, isopropanol, etc., is charged in an autoclave in a nitrogen stream, and from, 1/50 to 1/1000 mole of a ruthenium-optically active phosphine complex is added thereto per mole of the substrate. The hydrogenation reaction is effected at a temperature of from 25° to 50° C. at a hydrogen pressure of from 10 to 100 $kg/cm^2$ for a period of from 15 to 48 hours to thereby obtain an N-acyl-threonine. The resulting compound is then subjected to hydrolysis in a hydrochoric acid aqueous solution in a usual manner, followed by purification to obtain optically active threonine.

The present invention is now illustrated in greater detail with reference to Reference Examples and Examples, but it should be understood that the present invention is not deemed to be limited thereto.

REFERENCE EXAMPLE 1

Synthesis of $Ru_2Cl_4[(+)\text{-BINAP}]_2(NEt_3)$
(di[2,2'-bis(diphenylphosphino)-1,1'-binaphthyl]tetrachloro-diruthium triethylamine):

To 100 ml of toluene were added 1 g (3.56 mmoles) of $[RuCl_2(COD)]_n$, 2.66 g (4.27 mmoles of (+)-BINAP, and 1.5 g of triethylamine in a nitrogen atmosphere, and the mixture was heat-refluxed for 10 hours. The solvent was removed from the reaction mixture by distillation under reduced pressure, and the residual solid was dissolved in methylene chloride, followed by filtration through Celite. The filtrate was concentrated to dryness to obtain 3.7 g of the entitled compound as a deep brown solid.

Elemental Analysis for $C_{94}H_{79}Cl_4NP_4Ru_2$: Calcd. (%): Ru 11.96; C. 66.85; H 4.71; P 7.33. Found (%): Ru 11.68; C. 67.62; H 4.97; P 6.94.

$^1$H-NMR (CDCl$_3$) δ ppm: 1.30–1.50 (t, 6H, NCH$_2$CH$_3$), 3.05–3.30 (q, 4H, NCH$_2$CH$_3$). 6.40–8.60 (m, 32H, Ar-H)

REFERENCE EXAMPLE 2

Synthesis of $[Ru((-)\text{-T-BINAP})](ClO_4)_2$
([2,2'-bis(di-p-tolylphosphino)-1,1'-binaphthyl]ruthenium perchlorate)

In a 250 ml-volume Schlenk's tube was charged 0.54 g (0.30 mmole) of $Ru_2Cl_4[(-)\text{-T-BINAP}]_2(NEt_3)$. After thorough displacement of the atmosphere with nitrogen gas, 60 ml of methylene chloride was added thereto, and then a solution of 0.73 g (6.0 mmoles) of sodium perchlorate in 60 ml of water and a solution of 16 mg (0.06 mmole) of triethylbenzylammonium bromide in 3 ml of water were added to the mixture. The mixture was stirred at room temperature for 12 hours. After completion of the reaction, the reaction mixture was allowed to stand, and the aqueous layer was removed. The methylene chloride was removed from the organic layer by distillation under reduced pressure, and the residue was dried under reduced pressure to obtain 0.59 g (99.6%) of the entitled compound as a deep brown solid.

Elemental Analysis for $C_{48}H_{40}Cl_2P_2Ru$: Calcd. (%): Ru 10.32; C. 58.90; H 4.12; P 6.33. Found (%): Ru 10.08; C. 58.61; H 4.53; P 5.97.

$^{31}$P NMR (CDCl$_3$) δ ppm: 12.920 (d, J=41.1 Hz). 61.402 (d, J=41.1 Hz).

REFERENCE EXAMPLE 3

Synthesis of Ru[(−)-BINAP](OCOCH$_3$)$_2$ ([2,2'-bis(diphenyl-phosphino)-1,1'-binaphthyl]ruthenium-diacetate):

In a 250 ml-volume Schlenk's tube were charged 1.43 g (0.85 mmole) of Ru$_2$Cl$_4$[(−)-BINAP]$_2$(NEt$_3$) and 3.06 g (37 mmoles) of sodium acetate. After thorough displacement of the atmosphere with nitrogen, 100 ml of t-butanol was added thereto. The mixture was heated at reflux for 12 hours. After completion of the reaction, t-butanol was removed by distillation under reduced pressure of 20 mmHg, and the residual solid was extracted twice with 10 ml portions of ethyl ether. The ethyl ether was removed from the extract by distillation, and the resulting solid was further extracted twice with 10 ml portions of ethanol. The extract was concentrated to dryness to obtain 1.50 g of crude Ru[(−)-BINAP](OCOCH$_3$)$_2$. Recrystallization of the crude product from ethyl acetate gave 0.79 g (52%) of the entitled compound as a yellowish brown solid.

Melting Point: 180°–181° C. (with decomposition)
Elemental Analysis for $C_{48}H_{38}O_4P_2Ru$: Calcd. (%): Ru 12.01; C. 68.48; H 4.55; P 7.36. Found (%): Ru 11.85; C. 68.35; H 4.61; P 7.28.

31P-NMR (CDCl$_3$) δ ppm: 65.00 (s).
$^1$H-NMR (CDCl$_3$) δ ppm:
1.75 (s, 6H,

6.5–7.8 (m, 32H, naphthyl ring and phenyl proton).

REFERENCE EXAMPLE 4

Synthesis of [Ru((−)-T-BINAP)SnCl$_6$]$_2$NEt$_3$) (bis[ruthenium(2,2'-bis(di-p-tolylphosphino)-1,-.1)hexachlorotin]triethylamine):

In a 80 ml-volume Sohlenk's tube was charged 0.52 g (0.3 mmole) of Ru$_2$Cl$_4$[(−)-T-BINAP]$_2$(NEt$_3$). After thorough displacement of the atmosphere with nitrogen, 20 ml of methylene chloride and 0.16 g (0.6 mmole) of SnCl$_4$ were added thereto, followed by stirring at room temperature for 15 hours. After completion of the reaction, the methylene chloride was removed by distillation under reduced pressure, and the residue was dried to solidify to obtain 0.68 g (100%) of the entitled compound as a deep brown solid.

Elemental Analysis for $C_{102}H_{95}Cl_{12}NP_4Sn_2Ru_2$: Found (%): P 5.91; C. 53.48; H 4.36; Cl 17.56. Calcd. (%): P 5.33 C. 52.72; H4.12; Cl 18.31. $^{31}$P-NMR (CDCl$_3$) δ ppm: 14.14 (d, J=41.7 Hz). 62.57 (d, J=41.7 Hz).

In the foregoing Reference Examples, $^{31}$P-NMR spectra were measured by means of AM400 Model (161 MHz) manufactured by Bruker Co., and the chemical shift was determined by using 85% phosphoric acid as an external standard.

EXAMPLE 1

In a 500 ml-volume stainless steel autoclave whose atmosphere had been replaced with nitrogen was added a solution of 29 g (0.12 mole) of ethyl 2-N-benzamidoacetoacetate and 582 mg (0.33 mmole) of Ru$_2$Cl$_4$[(−)-BINAP]$_2$(NEt$_3$) prepared according to Reference Example 1 in 100 m; of methylene dichloride, and the solution was stirred at room temperature at a hydrogen pressure of 40 kg/cm$^2$ for 80 hours to effect hydrogenation. The solvent was removed by distillation, and the residue was subjected to silica gel column chromatography (eluent =7:3 mixture of hexane:isopropanol) to remove the catalyst and to obtain 23.0 g of N-benzoyl-D-threonine ethyl ester, which was crystallized from a 2'1 mixed solvent of ethyl ether and n-hexane to obtain 15.0 g of crystals. Recrystallization was from a 2:1 mixed solvent of benzene and ethyl ether to obtain 12.0 g (41.4%) of a pure product.

Melting Point: 85–86.5° C.
$[\alpha]_d{}^{25} = -29.5°$ (chloroform, c=3.225)

Then, 3.6 g of the resulting ester was refluxed in 10% hydrochloric acid for 3 hours to obtain a uniform solution. The solution was allowed to stand under ice-cooling for 1 hour, followed by filtration to remove benzoic acid crystals. The filtrate was concentrated to dryness, and the residue was dissolved in 10 ml of water. After adjusting to a pH of 7.0 with 28% aqueous ammonia, the solution was subjected to recrystallization from a 1:2 mixed solvent of water and ethanol to obtain 1.2 g (71%) of D-threonine.

$[\alpha]_D{}^{25} = +27.6°$ (H$_2$O, c=1.23).
Optical Yield: 97.2% ee.
$^1$H-NMR (D$_2$O) δ ppm: 4.18 (1H), 3.55 (1H, J=4.86 Hz), 1.25 (3H, J=6.78 Hz).

EXAMPLE 2

In a 500 ml-volume stainless steel autoclave whose atmosphere had been replaced with nitrogen was charged a solution of 20.7 g (0.11 mole) of ethyl 2-N-acetamidoacetoacetate and 444 mg (0.25 mmole) of Ru$_2$Cl$_4$[(−)-T-BINAP]$_2$(NEt$_3$) prepared according to Reference Example 1 in 200 ml of methylene dichloride, and the mixture was stirred at 50° C. at a hydrogen pressure of 100 kg/cm$^2$ for 24 hours to effect hydrogenation. The solvent was removed by distillation, and the residue was subjected to silica gel column chromatography (eluent =7:3 mixture of hexane and isopropanol) to remove the catalyst and to obtain 19.5 g (93%) of N-acetyl-D-threonine ethyl ester.

Then, 4.4 g of the resulting ester was refluxed in 10% hydrochloric acid for 3 hours to prepare a uniform solution. The solution was concentrated to dryness, and 10 ml of water was added to the residue. The solution was adjusted to a pH of 7 with 28% aqueous ammonia and then recrystallized from a 1:2 mixed solvent of water and ethanol to obtain 2.2 g (79%) of D-threonine.

$[\alpha]_D{}^{25} = +28.0°$ (H$_2$O c=1.85).
Optical Yield: 98.6%ee.
$^1$H-NMR (D$_2$O): The same as in Example 1.

EXAMPLE 3

In 50 ml of methanol were dissolved 17.3 g (0.1 mole) of methyl 2-N-acetamidoacetoacetate and 422 mg (0.25 mmole) of Ru$_2$Cl$_4$[(+)-BINAP]$_2$(NEt$_3$)as synthesized in Reference Example 1, and the solution was charged in an autoclave in a nitrogen stream. The solution was subjected to hydrogenation at 35° C. at a hydrogen pressure of 40 kg/cm² for 24 hours. The methanol was removed by distillation, and 72 ml of 10% hydrochloric acid was added to the residue, followed by heat-refluxing for 3 hours to obtain a uniform solution. The solution was concentrated to dryness, and 50 ml of water was added thereto. The solution was adjusted to a pH of 7 with 28% aqueous ammonia. The precipitated crystals were collected and dried to obtain 8.1 g (0.07 mol, 68%) of L-threonine.

$[\alpha]_D^{25} = -27.8°$ (H₂O, c=2.0).

Optical Yield: 97.9%ee.

EXAMPLE 4

In 50 ml of ethanol were dissolved 18.7 g (0.1 mole) of ethyl 2-N-acetamidoacetoacetate and 461 mg (0.5 mmole) of [Ru((+)-BINAP)](ClO₄)₂ prepared according to Reference Example 2, and the solution was charged in an autoclave in a nitrogen stream. The solution was subjected to hydrogenation at 25° C. and at a hydrogen pressure of 70 kg/cm² for 40 hours. The ethanol was removed from the reaction mixture by distillation under reduced pressure, and to the residue was added 70 ml of 10% hydrochloric acid, followed by heat-refluxing for 4 hours. The solution was concentrated to dryness, and 47 ml of water was added to the residue. The solution was adjusted to a pH of 7 with 28% aqueous ammonia, and the precipitated crystals were collected and dried to obtain 8.56 g (72%) of L-threonine.

$[\alpha]_D^{25} = -27°$ (H₂O c=1.5).

Optical Yield: 95%ee.

EXAMPLE 5

In 80 ml of ethanol were dissolved 28 g (0.1 mole) of ethyl 2-N-benzyloxycarbonylamidoacetoacetate and 1,105 mg (0.5 mmole) of [Ru((−)-BINAP)SnCl₆]₂.(NEt₃) as synthesized in Reference Example 4, and the solution was charged in an autoclave in a nitrogen stream. The solution was subjected to hydrogenation at 30° C. and at a hydrogen pressure of 50 kg/cm² for 30 hours. The ethanol was removed from the reaction mixture by distillation under reduced pressure, and 70 ml of 10% hydrochloric acid was added to the residue, followed by heat-refluxing for 3 hours. The solution was concentrated to dryness, and 50 ml of water was added to the residue. The solution was adjusted to a pH of 7 with 28% aqueous ammonia. The thus precipitated crystals were collected and dried to obtain 8.33 g (70%) of D-threonine.

$[\alpha]_D^{25} = +25.6°$ (H₂O c=2.1).

Optical Yield: 90%ee.

EXAMPLE 6

In 54 ml of ethanol were dissolved 18.7 g (0.1 mole) of ethyl 2-N-acetamidoacetoacetate and 89.7 g (0.1 mmole) of Ru[(−)-T-BINAP](OCOCH₃)₂ prepared according to Reference Example 3, and the solution was charged in an autoclave in a nitrogen stream. The solution was subjected to hydrogenation at 30° C. and at a hydrogen pressure of 70 kg/cm² for 35 hours. The ethanol was removed from the reaction mixture by distillation, and to the residue was added 70 ml of 10% hydrochloric acid, followed by heat-refluxing for 3 hours. The solution was concentrated to dryness. To the residue was added 50 ml of water, and the solution was adjusted to a pH of 7 with 28% aqueous ammonia. The precipitated crystals were collected and dried to obtain 8.9 g (72%) of D-threonine.

$[\alpha]_D^{25} = +27°$ (H₂O c=1.7).

Optical Yield: 88%ee.

EXAMPLES 7 to 14

The same procedure of Examples 1 to 6 was repeated, except for altering the substrate, catalyst and reaction conditions as shown in Table 1. The reaction results are shown in Table 1.

TABLE 1

| Example No. | Substrate | Catalyst | Substrate Catalyst mole/mole | Reaction Conditions | | | | Reaction Product | | |
|---|---|---|---|---|---|---|---|---|---|---|
| | | | | Solvent | Hydrogen Pressure (kg/cm$^2$) | Temperature (°C.) | Time (hr) | Yield (%) | Optical Rotation $[\alpha]_D^{25}$ (°) | Optical Yield (% ee) |
| 7 | benzyl 2-N—acetamidoacetoacetate | Ru$_2$Cl$_4$[(+)-BINAP]$_2$(NEt$_3$) | 50 | methylene chloride | 70 | 30 | 15 | 93 | −26.4 | 93 |
| 8 | benzyl 2-N—benzyloxycarbonylamidoacetoacetate | Ru$_2$Cl$_4$[(−)-T-BINAP]$_2$-(NEt$_3$) | 100 | ethanol | 50 | 25 | 24 | 95 | +27.0 | 95 |
| 9 | methyl 2-N—t-butyloxycarbonylamidoacetoacetate | Ru$_2$Cl$_4$[(−)-BINAP]$_2$(NEt$_3$) | 200 | methanol | 45 | 25 | 40 | 98 | +27.8 | 98 |
| 10 | ethyl 2-N—ethoxycarbonylamidoacetoacetate | Ru$_2$Cl$_4$[(−)-BINAP]$_2$(NEt$_3$) | 200 | ethanol | 45 | 25 | 40 | 93 | +25.8 | 91 |
| 11 | methyl 2-N—acetamidoacetoacetate | Ru[(−)-T-BINAP](OCOCF$_3$)$_2$ | 100 | methanol | 60 | 30 | 24 | 94.5 | +25.27 | 89 |
| 12 | methyl 2-N—acetamidoacetoacetate | Ru[(−)-t-Bu-BINAP](OCOCH$_3$)$_2$ | 50 | methanol | 70 | 30 | 30 | 94.7 | +24.13 | 85 |
| 13 | methyl 2-N—acetamidoacetoacetate | [Ru(+)-BINAP)](BF$_4$)$_2$ | 100 | methanol | 50 | 25 | 24 | 95.1 | −26.11 | 92 |
| 14 | methyl 2-N—acetamidoacetoacetate | [Ru((−)-T-BINAP)ZnCl$_4$]$_2$-(NEt$_3$) | 100 | methanol | 65 | 25 | 24 | 94 | +27.25 | 96 |

As described above, the present invention provides a process for preparing optically active threonine, which is important as an essential amino acid and also useful as an intermediate for pharmaceuticals, by asymmetric hydrogenation of a 2-N-acylaminoacetoacetic ester using a cheap ruthenium-optically active phosphine complex as a catalyst and then hydrolyzing the product. According to the present invention, either of natural type threonine or non-natural type threonine can be selectively synthesized by selecting the absolute configuration of the ligand of the ruthenium-optically active phosphine complex. Therefore, the process of the present invention is industrially superior.

While the invention has been described in detail and with reference to specific embodiments thereof, it will be apparent to one skilled in the art that various changes and modifications can be made therein without departing from the spirit and scope thereof.

What is claimed is:

1. A process for preparing optically active threonine which comprises asymmetrically hydrogenating a 2-N-acylaminoacetoacetic ester represented by formula (I):

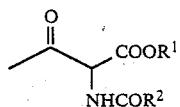
(I)

wherein $R^1$ represents a lower alkyl group, a phenyl group, a phenyl group substituted with a lower alkyl group or a lower alkoxy group, a benzyl group, or a benzyl group substituted with a lower alkyl group or a lower alkoxy group; $R^2$ represents a hydrogen atom, a lower alkyl group, a lower alkoxy group, a phenyl group, a phenyl group substituted with a lower alkyl group or a lower alkoxy group, a benzyloxy group, or a benzyloxy group substituted with a lower alkyl group or a lower alkoxy group, in the presence of a ruthenium-optically active phosphine complex as a catalyst to obtain an optically active threonine derivative represented by formula (II):

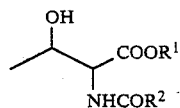
(II)

wherein $R^1$ and $R^2$ are as defined above, and then hydrolyzing the compound of formula (II).

2. A process as claimed in claim 1, wherein said ruthenium-optically active phosphine complex is selected from a compound represented by formula (III):

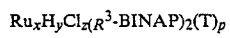
(III)

wherein $R^3$-BINAP represents a tertiary phosphine represented by formula (IV):

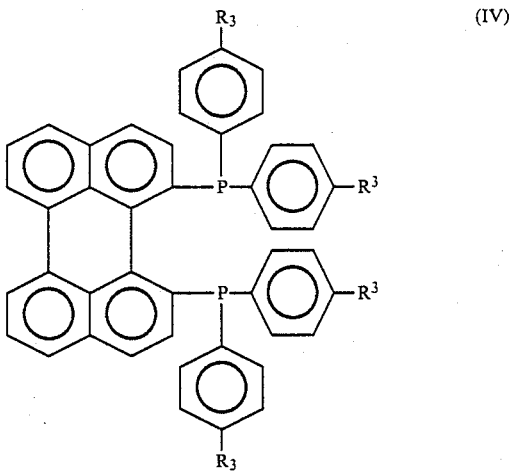
(IV)

wherein $R^3$ represents a hydrogen atom, a methyl group, or a t-butyl group; T represents a tertiary amine; when y represents 0, x represents 2, z represents 4, and p represents 1; and when y represents 1, x represents 1, l represents 1, and p represents 0, a compound represented by formula (V):

(V)

wherein $R^3$-BINAP is as defined above; Y represents $ClO_4$, $BF_4$ or $PF_6$; when u represents 0, v represents 1, and w represents 2; and when u represents 1, v represents 2, and w represents 1, a compound represented by formula (VI):

(VI)

wherein $R^3$-BINAP is as defined above; and $R_4$ represents a lower alkyl group or a trifluoromethyl group, and a compound represented by formula (VII):

(VII)

wherein $R^3$-BINAP is as defined above; M represents Zn, Al, Ti, or Sn; X represents $N(C_2H_5)_3$ or $CH_3CO_2$; when X is $N(C_2H_5)_3$, l is 2, m is 1, and k is 4 when M is Zn, 5 when M is Al, or 6 when M is Ti or Sn; and when X is $CH_3CO_2$, l is 1, m is 2, and k is 2 when M is Zn, 3 when M is Al, or 4 when M is Ti or Sn.

* * * * *